United States Patent
Takahashi et al.

(10) Patent No.: US 6,602,928 B2
(45) Date of Patent: Aug. 5, 2003

(54) PACKING MATERIAL AND CARTRIDGE FOR SOLID PHASE EXTRACTION

(75) Inventors: Ryuji Takahashi, Kanagawa (JP); Kuniko Igarashi, Kanagawa (JP); Hiroshi Suzuki, Kanagawa (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 2 days.

(21) Appl. No.: 09/932,994

(22) Filed: Aug. 21, 2001

(65) Prior Publication Data

US 2002/0041938 A1 Apr. 11, 2002

Related U.S. Application Data

(60) Provisional application No. 60/244,659, filed on Nov. 1, 2000.

(30) Foreign Application Priority Data

Aug. 21, 2000 (JP) .................................... P2000-249740
Oct. 2, 2000 (JP) .................................... P2000-301833

(51) Int. Cl.$^7$ ................................................ C08F 36/00
(52) U.S. Cl. ........................ 521/150; 521/56; 521/60; 526/149; 526/303.1; 526/307.1; 526/307.7; 526/323.1; 526/323.2; 526/336
(58) Field of Search ........................ 521/56, 149, 150, 521/60; 526/303.1, 307.1, 307.7, 323.1, 323.2, 336

(56) References Cited

U.S. PATENT DOCUMENTS 5,795,709 A * 8/1998 Adegawa et al. ........... 430/627
6,362,245 B1 * 3/2002 Takahasshi ................. 521/149

FOREIGN PATENT DOCUMENTS

JP 6-258203 * 9/1994

* cited by examiner

Primary Examiner—Helen L. Pezzuto
(74) Attorney, Agent, or Firm—Sughrue Mion, PLLC

(57) ABSTRACT

A packing material for solid phase extraction, which is a particle having an exclusion limit molecular weight of $1 \times 10^3$ to $1.5 \times 10^4$ in gel permeation chromatography using a standard polystyrene as the sample. A column for solid phase extraction and a cartridge for solid phase extraction, a method of using the packing material; and a process for treating a sample using the column or cartridge are also disclosed.

15 Claims, No Drawings ly invention provides the
PACKING MATERIAL AND CARTRIDGE FOR SOLID PHASE EXTRACTION

CROSS REFERENCE TO RELATED APPLICATIONS

This application is an application filed under 35 U.S.C. §111(a) claiming benefit pursuant to 35 U.S.C. §119(e)(1) of the filing date of Provisional Application 60/244,659 filed Nov. 1, 2000 pursuant to 35 U.S.C. §111(b).

FIELD OF THE INVENTION

The present invention relates to a packing material for solid phase extraction, which has a specific exclusion limit molecular weight or a specific pore size; a column and a cartridge for solid phase extraction, each using the packaging material; and a process for treating a medical sample, which uses the column or cartridge.

BACKGROUND OF THE INVENTION

In many cases, a liquid-liquid extraction method has been heretofore used for extracting a sample from a liquid, however, this method has a problem in that the operation is cumbersome, a solvent is used in a large amount and the solvent used greatly affects the environment and the human body. In recent years, with the progress of synthesis methods, a solid phase extraction method using silica-type or synthetic polymer-type porous particles capable of treating a large amount of sample through a simple operation using a small amount of solvent by virtue of automation has been used.

The packing material for use in the solid phase extraction is an inorganic substrate such as silica gel or chemical bonding-type silica gel obtained by chemically modifying the surface of silica gel, or an organic substrate such as a synthetic polymer-type substrate represented by polystyrene-divinylbenzene or a substrate obtained by chemically modifying the surface thereof.

Heretofore, inorganic or organic packing materials are known to be used in the solid phase extraction. For example, JP-A-6-258203 (the term "JP-A" as used herein means an "unexamined published Japanese patent application") describes a cartridge column for solid phase extraction, which is packed with a copolymer of divinylbenzene and polyhydric alcohol poly(meth)acrylic acid ester. However, in this patent publication, only the hydrophobicity and hydrophilicity on the surface of the crosslinked copolymer particle are discussed.

As such, only the chemical properties, such as hydrophobicity or hydrophilicity on the particle surface, of the packing material for solid phase extraction has been studied, but studies on the physical properties such as pore size distribution have not been satisfactorily made.

SUMMARY OF THE INVENTION

An object of the present invention is to obtain a packing material having excellent properties based on the physical properties such as pore size range of the packing material while taking account of the chemical properties such as hydrophobicity or hydrophilicity on the particle surface of conventional packing materials for solid phase extraction.

As a result of extensive investigations to overcome the above-described problems, the present inventors have found that a packing material for solid phase extraction, which ensures excellent recovery of a sample can be obtained by controlling the pore size distribution. The present invention has been accomplished based on this finding.

More specifically, the present invention provides to the following embodiments.

[1] A packing material for solid phase extraction, comprising particles having an exclusion limit molecular weight of from $1 \times 10^3$ to $1.5 \times 10^4$ in gel permeation chromatography using a standard polystyrene as the measuring sample.

[2] The packing material for solid phase extraction as described in [1] above, wherein the particle is a synthetic polymer particle obtained by polymerizing monomers containing at least a crosslinkable monomer.

[3] The packing material for solid phase extraction as described in [2] above, wherein the synthetic polymer particle is a polymer of at least a crosslinkable monomer (A) and a non-crosslinkable monomer (B).

[4] The packing material for solid phase extraction as described in [3] above, which contains an aromatic divinyl compound as the crosslinkable monomer (A) in an amount of 30% by mass or more based on the total amount of monomers.

[5] The packing material for solid phase extraction as described in [3] or [4] above, which contains a polyhydric alcohol poly(meth)acrylic acid ester as the crosslinkable monomer (A) in an amount of 10% by mass or more based on the total amount of monomers.

[6] The packing material for solid phase extraction as described in any one of [3] to [5] above, which contains an N-vinylcarboxylic acid amide as the non-crosslinkable monomer (B) in an amount of 5 to 60% by mass based on the total amount of monomers.

[7] The packing material for solid phase extraction as described in [6] above, wherein the N-vinylcarboxylic acid amide is N-vinylacetamide.

[8] The packing material for solid phase extraction as described in any one of [1] to [7] above, which is packed into a column, a cartridge or a reservoir on use.

[9] The packing material for solid phase extraction as described in any one of [1] to [8] above, which is used for concentrating an objective component and/or removing impurities or contaminants.

[10] The packing material for solid phase extraction as described in any one of [1] to [9] above, which has an average particle size of 1 to 200 μm.

[11] A column for solid phase extraction] above, which is packed with the packing material for solid phase extraction described in any one of [1] to [10] above.

[12] A cartridge for solid phase extraction] above, which is packed with the packing material for solid phase extraction described in any one of [1] to [10].

[13] The column for solid phase extraction as described in [11] above, which is used for concentrating an objective component and/or removing impurities or contaminants.

[14] The cartridge for solid phase extraction as described in [12] above, which is used for concentrating an objective component and/or removing impurities or contaminants.

[15] A process for treating an environment- or medical sample, which uses the column for solid phase extraction described in [11] or [13] above.

[16] A process for treating an environment- or medical sample, which uses the cartridge for solid phase extraction described in [12] or [14] above.

[17] The process for treating an environment- or medical sample as described in [15] or [16] above, which is used for the treatment of a protein component-containing sample.

DESCRIPTION OF THE INVENTION

The packing material for solid phase extraction of the present invention is a particle having an exclusion limit molecular weight of from $1\times10^3$ to $1.5\times10^4$, preferably $7\times10^3$ to $1.5\times10^4$, in gel permeation chromatography using a standard polystyrene as the measuring sample. The surface area of the particles is 350 to 800 $m^2/g$, preferably 450 to 700 $m^2/g$ and more preferably 550 to 670 $m^2/g$. This particle may use an inorganic substrate or an organic substrate, however, a synthetic polymer-type packing material for solid phase extraction using an organic substrate is preferred when taking into account the easiness of bulk synthesis, good reproduction in the control of pore size and the like. Examples of the synthetic polymer using an organic substrate include polystyrene-divinylbenzene type; poly(meth)acrylate type such as polyacrylate, glycidyl methacrylate and ethylene glycol dimethacrylate, and various copolymers thereof.

In the present invention, the packing material for solid phase extraction is preferably obtained by polymerizing monomers containing at least a crosslinkable monomer (A) or by copolymerizing a crosslinkable monomer (A) and a non-crosslinkable monomer (B). The packing material for solid phase extraction of the present invention includes polymers obtained by polymerizing only the crosslinkable monomer (A) as the monomer without containing the non-crosslinkable monomer (B). The crosslinkable monomer (A) for use in the present invention is not particularly limited as long as it polymerizes with a monomer used and examples thereof include aromatic compounds having two or more vinyl groups, such as divinylbenzene, divinyltoluene, divinylxylene and divinylnaphthalene; and polyhydric alcohol poly(meth)acrylic acid esters such as ethylene glycol di(meth)acrylate, polyethylene glycol di(meth)acrylate, propylene glycol di(meth)acrylate, polypropylene glycol di(meth)acrylate, glycerin di(meth)acrylate, trimethylolpropane tri(meth)acrylate, tetramethylolmethane tri(meth)acrylate and tetramethylolmethane tetra(meth)acrylate.

The aromatic compound having two or more vinyl groups, such as divinylbenzene, divinyltoluene, divinylxylene and divinylnaphthalene, is preferably contained in an amount of 30% by mass or more, more preferably 45% by mass or more, based on the total amount of monomers. Among these aromatic compounds having two or more vinyl groups, divinylbenzene is preferably used in view of easy availability.

The purity of the aromatic compound having two or more vinyl groups, such as divinylbenzene, used in the present invention is not particularly limited, however, an aromatic compound having a purity of 55% by mass or more is preferably used.

In the present invention, a polyhydric alcohol poly(meth)acrylic acid ester can also be used as the crosslinkable monomer (A). Among polyhydric alcohol poly(meth)acrylic acid esters, ethylene glycol di(meth)acrylate and glycerin di(meth)acrylate are preferred when taking into account the reactivity, operability during the reaction and the balance of swelling degree in the copolymer particles produced. The polyhydric alcohol poly(meth)acrylic acid ester is preferably contained in an amount of 10% by mass or more, more preferably from 20 to 25% by mass, based on the total amount of monomers.

Examples of the non-crosslinkable monomer (B) for use in the present invention include N-vinylcarboxylic acid amides such as N-vinylformamide, N-vinylacetamide, N-vinylpropionamide, N-(propeny-2-yl)formamide and N-(propenyl-2-yl)acetamide. Among these, in view of the hydrophilicity and the operability during the reaction, N-vinylacetamide is preferably used. The N-vinylacetamide is contained in an amount of 5 to 60% by mass, preferably from 5 to 30% by mass, based on the total amount of monomers.

The packing material for solid phase extraction of the present invention is porous and for the purpose of imparting the porosity, a diluent is added to a mixture of monomers during the polymerization. The diluent that can be used is an organic solvent having properties so that it dissolves in the monomer mixture, is inactive to the polymerization reaction and does not dissolve the polymer produced. Examples thereof include aromatic hydrocarbons such as toluene, xylene, ethylbenzene and diethylbenzene; saturated hydrocarbons such as hexane, heptane, octane and decane; alcohols such as isoamyl alcohol, hexyl alcohol, octyl alcohol and 2-ethylhexyl alcohol; aliphatic halogenated hydrocarbons such as dichloromethane, dichloroethane and trichloroethane; and aliphatic or aromatic esters such as ethyl acetate, butyl acetate, dimethyl phthalate and diethyl phthalate. These organic solvents used as a diluent can be used individually or in combination of two or more thereof.

In the case of a copolymer having a pore size so that the exclusive limit molecular weight in gel permeation chromatography using a standard polystyrene as the sample is from $1\times10^3$ to $1.5\times10^4$, toluene or a mixture of toluene and an alcohol such as 2-ethylhexyl alcohol is preferably used.

The amount of the diluent added is preferably from 10 to 300% by mass based on the total amount of the crosslinkable monomer (A) and the non-crosslinkable monomer (B), and in the case of a copolymer having a pore size so that the exclusive limit molecular weight for polystyrene in gel permeation chromatography is from $1\times10^3$ to $1.5\times10^4$, the amount of the diluent added is preferably from 50 to 150% by mass.

The copolymer particle of the present invention is produced by suspension polymerization in an aqueous medium containing an appropriate dispersion stabilizer. In this case, the polymerization initiator used is not particularly limited as long as it is a known radical polymerization initiator capable of generating a radical, and examples thereof include azo-type initiators such as 2,2'-azobisisobutyronitrile and 2,2'-azobis(2,4-dimethylvaleronitrile). The concentration of the polymerization initiator is preferably from 0.1 to 5% by mass based on the monomers.

In the present invention, the polymerization reaction can be performed by the suspension polymerization method where a monomer solvent containing a diluent is stirred in an aqueous medium containing an appropriate dispersion stabilizer and suspended and then the polymerization is allowed to proceed. The dispersion stabilizer may be a known dispersion stabilizer, and in general, a water-soluble polymer compound such as gelatin, sodium polyacrylate, poly(vinyl alcohol), hydroxyethyl cellulose or carboxymethyl cellulose is used. The concentration of the dispersion stabilizer used is preferably from 0.1 to 5% by mass based on the aqueous medium. The aqueous medium is a medium mainly comprising water and in the medium, a salt and other water-soluble components may be dissolved in addition to water.

The polymerization reaction is preferably performed by dissolving a salt in the aqueous medium for the purpose of suppressing the monomers from dissolving in the aqueous medium. Examples of the salts used include sodium chloride, calcium chloride and sodium sulfate.

The N-vinylcarboxylic acid amide has a high solubility in water, and therefore, a salt is preferably used in a high concentration to suppress the dissolution. The salt used and the concentration thereof are not particularly limited, but since the solubility varies depending on the salt used, for example, sodium chloride is preferably used in an amount of 0.1 to 15% by mass and calcium chloride is preferably used in an amount of 1 to 40% by mass, based on the aqueous medium.

If the mass ratio (liquid ratio) of (1) the aqueous dispersion medium phase containing a dispersion stabilizer and a salt to (2) the organic solvent phase formed by mixing a monomer mixture containing the crosslinkable monomer (A) and the non-crosslinkable monomer (B) with a diluent and dissolving a polymerization initiator therein is excessively large, the N-vinylcarboxylic acid amide is distributed into the aqueous dispersion medium phase because of its high solubility in water and the yield decreases. On the other hand, if the liquid ratio is too small, the suspension dispersion of the organic solvent phase becomes unstable. Accordingly, the ratio of the aqueous dispersion phase to the organic solvent phase is preferably from 2:1 to 10:1.

The polymerization reaction is performed, after purging with nitrogen gas, by heating the reaction system to 40 to 100° C. with ordinary stirring for 5 to 16 hours under an atmospheric pressure. The organic solvent phase becomes spherical particles as a result of the stirring and the particles disperse in the aqueous medium, whereby the reaction proceeds. At this time, the polymerization proceeds in the state so that individual particles contain a diluent, and the polymer grows as a network polymer. As a result, when the diluent is removed later, porous particles can be obtained.

After the reaction, the particles can be easily separated by filtration or the like and the diluent can be easily removed through washing with a solvent such as acetone or methanol and then drying. The thus-obtained packing material having a pore size controlled to a specific range is classified into a particle size of 1 to 200 $\mu$m, preferably from 1 to 100 $\mu$m, more preferably from 20 to 70 $\mu$m, and then used as a packing material for solid phase extraction.

The packing material for solid phase extraction of the present invention can be widely applied to the concentration or removal of trace components and in particular, can be used by packing it into a reservoir of a column or a cartridge.

In the solid phase extraction method, the packing material manufactured for use in the solid phase extraction is used by packing it into a container called a reservoir of a column or a cartridge. However, the shape and the constructive material of the container such as column, cartridge and reservoir are not particularly limited as long as the container is insoluble in the organic solvent used and impurities do not dissolve out from the container itself during the operation of solid phase extraction.

In the present invention, the cartridge means a cylindrical container having an internal diameter of 2 to 6 mm$\phi$ and a length of 10 to 30 mm, where both ends are stopped by a frit or a filter to prevent flowing out of gel and the frit or filter is fastened by a cap having a hole of 0.1 to 1 mm in the center. The cartridge by itself has no connector necessary for flowing a liquid and therefore, is used by fixing it to an exclusive cartridge holder, guard holder or reservoir container called holder.

The column is a cylindrical container having an internal diameter of 2 to 6 mm$\phi$ and a length of from 10 to 50 mm with both ends stopped by an end-fitting. The end-fitting has a connector together with a frit or a filter for preventing the flowing out of gel. Therefore, the column means a container which can be directly connected to allow the flowing of a liquid.

Examples of the constructive material for the cartridge or column include inorganic materials such as stainless steel and glass, and synthetic resin materials such as polyethylene, polypropylene and polyether ether ketone. Among these, on considering simplicity, convenience and cost, a polyethylene-made container is preferred and examples thereof include an injector-type container having a volume of 1 to 200 mL, preferably from 1 to 100 mL.

In the column or cartridge for solid phase extraction, a porous plate called a filter or frit having a pore of 5 to 200 $\mu$m, preferably from 10 to 50 $\mu$m, is set to both ends of the column or reservoir to prevent the passing through of the packing material during the operation of solid phase extraction. The constructive material of the filter or frit is not particularly limited but examples thereof include stainless steel, glass, polyethylene and polytetrafluoroethylene. Among these, polyethylene is preferred in view of the cost and operability.

The amount of the packing material for solid phase extraction packed in the reservoir of column or cartridge varies depending on the bulk density of particles or the concentration ratio of the sample. However, the amount packed is usually from 30 to 500 mg, preferably from 50 to 300 mg, based on the volume of 3 mL in each case.

Use of the column or cartridge packed with the packing material for solid phase extraction of the present invention is not particularly limited. However, in view of the properties of the packing material for solid phase extraction, the column or cartridge can be used for concentrating a trace objective substance contained in an extra dilute solution and/or for easily removing impurities or contaminants present together, during analysis treatment of an environment-related sample, a medical sample or the like. Furthermore, the column or cartridge can be suitably used for the measurement of harmful substances such as agricultural chemicals in river water, the measurement of residual agricultural chemicals in farm products and the measurement of drugs in serum. The column or cartridge is effective, for example, in the adsorption and removal of albumin and the like, however, the use is not limited thereto.

The process for treating an environment-related sample or a medical sample of the present invention is a solid phase extraction process where an objective component is extracted in the solid phase using the above-described packing material and/or column or cartridge for solid phase extraction. The treating process of the present invention is to concentrate a trace objective substance contained in an extra dilute solution and/or remove impurities or contaminants present together during the analysis of various samples and can be applied as a pretreatment and/or a post-treatment in various analyses.

EXAMPLES

The present invention is described in greater detail below by referring to the Examples, however, the present invention is by no means limited to these Examples. Unless indicated otherwise herein, all parts, percents, ratios and the like are by weight.

Example 1

18.75 g of pulverized N-vinylacetamide (NVA monomer, produced by Showa Denko K.K.) was dissolved in a mixed solution of a monomer phase containing 41.25 g of divinylbenzene having a purity of 81% (DVB-H, produced by Sankyo Kasei K.K.) and 15.00 g of ethylene glycol dimethacrylate (NK Ester 1G, produced by Shin Nakamura Kagaku Kogyo K.K.) and a diluent phase containing 30.28 g of toluene (produced by Wako Junyaku Kogyo K.K.) and 10.10 g of 2-ethylhexanol (produced by Wako Junyaku Kogyo K.K.) and subsequently, 2.00 g of 2,2'-azobis(2,4-dimethylvaleronitrile) was dissolved therein to prepare an oil phase.

In 286 mL of deionized water, 103.5 g of calcium chloride and 10.35 g of sodium chloride were dissolved to prepare a salt solution. Subsequently, 4 g of polyvinyl alcohol (Kuraray Poval PVA-224, produced by Kuraray K.K.) and 4 g of sodium chloride were dissolved in 100 mL of deionized water and therefrom, 86 mL was sampled and added to the salt solution. Furthermore, 6.4 mg of sodium nitrite was dissolved in 10 mL of deionized water and therefrom, 7 mL was sampled and added into the salt solution. The thus-prepared salt solution was used as the aqueous phase.

The oil phase and the aqueous phase were mixed and stirred at a high speed of 1,800 rpm for 5 minutes in Excel Auto Homogenizer (produced by Nihon Seiki Seisakusho K.K.) to adjust the oil droplets to from 20 to 100 μm. Thereafter, the suspension was poured into 1 L-volume separable flask and reacted for 6 hours by elevating the temperature to 70° C. while stirring at 100 rpm in a water bath in a nitrogen gas atmosphere. After cooling, the copolymer particles produced were separated by filtration through a filter paper of No. 101, washed with 2 L of deionized water and with 2 L of acetone, then air-dried by spreading the particles on a stainless steel-made vat, and further dried under reduced pressure at 60° C. for 16 hours. The copolymer particles obtained were classified into from 40 to 70 μm using a pneumatic classifier (MINI. CLASSIFIER, manufactured by NIPPON PNEUMATIC MFG) to prepare a packing material for solid phase extraction.

Measurement of Exclusion Limit Molecular Weight by Gel Permeation Chromatography Using a packer and a pump, the copolymer particles classified into from 40 to 70 μm were packed into a stainless steel-made column for liquid chromatography of 4.6 mm (inside diameter)×150 mm (length) by an equilibrium slurry method to obtain a packed column. This column was connected to a high performance liquid chromatograph, tetrahydrofuran as a mobile phase was flowed at a flow rate of 0.33 ml/min, and then standard polystyrene Standards (Shodex (registered trade mark of Showa Denko) STANDARD S series, dealing by Showa Denko K.K.) having an average molecular weight of 2,400,000, 1,070,000, 460,000, 156,000, 66,000, 28,500, 11,600, 7,000, 5,050, 3,250, 2,450, 1,680, 1,320, 980 or 580 and benzene was each injected. An elution time was determined from the chromatogram obtained and an exclusion limit molecular weight was measured by plotting the logarithm of average molecular weight for the ordinate and the elution time for the abscissa on a graph.

The exclusion limit molecular weight obtained was 7,000. The measurement of the surface area was performed using COULTER SA3100 manufactured by COULTER, and as a result, the surface area of the copolymer particles was 635 $m^2/g$.

250 mg of copolymer particles classified into from 40 to 70 μm were packed in a 3 mL-volume reservoir to prepare a cartridge for solid phase extraction and the measurement of recovery was performed according to the following procedure.

1. The cartridge for solid phase extraction was set to a suction manifold.
2. 5 mL of acetonitrile was passed at 5 ml/min.
3. 5 mL of deionized water was passed at 5 ml/min.
4. 100 mL of a sample adjusted to 0.25 ppm as a sample for concentration was passed at 5 mL/min and the sample was concentrated (adsorbed) in the cartridge for solid phase extraction.
5. 5 mL of deionized water was passed at 5 ml/min.
6. 5 mL of acetonitrile was passed at 5 ml/min and the eluate was recovered.
7. From the recovered eluate, 20 μl was sampled and analyzed by a high performance liquid chromatograph and the area value thereof was determined.
8. Using as the standard sample the same substance used for the sample adsorbed, 20 μl of a sample was adjusted to 5 ppm and analyzed by a high performance liquid chromatograph and the area value thereof was determined.
9. The recovery was obtained by the area value of the sample for concentration/ the area value of the standard sample.

If the copolymer has a low capability of concentration, the sample is not adsorbed to the copolymer and the recovery decreases. The results of the measurement of recovery are shown in Table 1. The recovery was 85% or more and from this, it was revealed that the copolymer was a packing material for solid phase extraction having an excellent capability of concentrating a sample.

Example 2

A copolymer was synthesized in the same manner as in Example 1 except for changing the diluent phase to 37.50 g of toluene and 12.50 g of 2-ethylhexanol. The measurements of the exclusion limit molecular weight by gel permeation chromatography, the surface area and the recovery by solid phase extraction were also performed in the same manner as in Example 1. The exclusion limit molecular weight obtained was 15,000, the surface area was 601 $m^2/g$. As a result, as seen in Table 1, it was revealed that the copolymer was a packing material for solid phase extraction having an excellent capability of concentrating a sample, similar to Example 1.

Comparative Example 1

A copolymer was synthesized and evaluated in the same manner as in Example 1, except for changing the diluent phase to 49.90 g of toluene and 16.60 g of 2-ethylhexanol. The exclusion limit molecular weight obtained by gel permeation chromatography was 25,000 and the surface area was 643 $m^2/g$. As seen from the results of measurement of the recovery by solid phase extraction shown in Table 1, the recovery was low and the copolymer was a packing material for solid phase extraction having a low capability of concentrating a sample.

Comparative Example 2

A copolymer was synthesized and evaluated in the same manner as in Example 1, except for changing the diluent phase to 77.91 g of toluene and 13.75 g of 2-ethylhexanol. The exclusion limit molecular weight obtained by gel permeation chromatography was 60,000 and the surface area was 788 $m^2/g$. As seen from the results in Measurement 1 of Recovery by Solid Phase Extraction shown in Table 1, the recovery was low and the copolymer was a packing material for solid phase extraction having a low capability of concentrating a sample.

TABLE 1

| | Recovery (%) | | | |
|---|---|---|---|---|
| | Example 1 | Example 2 | Comparative Example 1 | Comparative Example 2 |
| Phenol | 101.7 | 87.2 | 59.0 | 53.8 |
| o-Chlorophenol | 100.8 | 87.0 | 57.4 | 50.9 |
| m-Chlorophenol | 99.0 | 87.9 | 55.6 | 48.5 |
| p-Chlorophenol | 100.4 | 88.5 | 55.8 | 50.0 |

Conditions for High Performance Liquid Chromatography

| | |
|---|---|
| Column: | Shodex (registered trade mark of Showa Denko K.K.) C18-5A (4.6 mm$\phi$ × 150 mm) |
| Mobile phase: | acetonitrile/water = 40/60 (V/V) |
| Flow rate: | 1.0 mL/min |
| Detector: | ultraviolet absorption detector |
| Measuring wavelength: | UV 254 nm |
| Amount of sample injected: | 20 $\mu$L |

Example 3

The copolymer particles (exclusion limit molecular weight: 7,000) obtained in Example 1 were classified into from 40 to 70 $\mu$m, 50 mg thereof was packed in a 1 mL-volume reservoir to prepare a cartridge for solid phase extraction, and the measurement of recovery was performed according to the following procedure.

Measurement 2 of Recovery by Solid Phase Extraction

1. The cartridge for solid phase extraction was set to a suction manifold.
2. 1 mL of methanol was passed at 1 ml/min.
3. 1 mL of 50 mM sodium phosphate buffer solution (pH 6.0) was passed at 1 ml/min.
4. Samples for concentration obtained by dissolving ketoprofen, pindolol and prednisolone into 2 mL of 50 mM sodium phosphate buffer solution (pH 6.0) containing 20 mg of bovine serum albumin to a concentration of 0.2 ppm, 0.5 ppm and 1.0 ppm, respectively, each was passed at 1 ml/min and concentrated (adsorbed) in the cartridge for solid phase extraction.
5. 1 mL of 50 mM sodium phosphate buffer solution (pH 6.0) containing 5% of methanol was passed at 1 mL/min to perform the cleaning.
6. 1 mL of methanol was passed at 1 mL/min and the eluate was recovered.
7. From the recovered eluate, 20 $\mu$l was sampled and analyzed by a high performance liquid chromatograph 1 or 2 and the area value was determined.
8. Using as the standard sample the same substance as used for the sample adsorbed, 20 $\mu$l of a sample was adjusted to 0.2 ppm, 1.0 ppm and 2.0 ppm, respectively, and analyzed by the high performance liquid chromatograph 1 and the area value thereof was determined.
9. 20 $\mu$L of a standard sample of 50 mM sodium phosphate buffer solution (pH 6.0) containing 10 mg/mL of bovine serum albumin was analyzed by the high performance liquid chromatograph 2 and the area value thereof was determined.
10. From the area value of the sample for concentration/the area value of the standard sample, the recovery of each drug and the adsorption ratio (removal ratio) of bovine serum albumin were determined.

Comparative Example 3

Using a commercially available solid phase cartridge in which 50 mg of octadecyl silica (exclusion limit molecular weight: 100,000) having a particle size of 40 to 70 $\mu$m was packed into a 1 mL-volume reservoir, the same operation as in Example 3 was performed, and the recovery of each drug and the adsorption ratio (removal ratio) of albumin were determined.

In Example 3, it was verified that three kinds of drugs were effectively concentrated and recovered, and at the same time, albumin as high molecular weight impurities or contaminants was mostly prevented from adsorbing.

On the other hand, in Comparative Example 3, recovery of some acidic or basic drugs was low and, importantly, bovine serum albumin slightly adsorbed, revealing that a problem was present from the standpoint of pretreating a sample.

TABLE 2

| | Recovery and Adsorption Ratio (%) | |
|---|---|---|
| | Example 3 | Comparative Example 3 |
| Ketoprofen | 89.4 | 62.0 |
| Pindolol | 90.2 | 51.5 |
| Prednisolone | 88.0 | 86.8 |
| Bovine serum albumin | 0.1 | 2.5 |

Conditions for Measurement by High Performance Chromatograph 1

| | |
|---|---|
| Column: | Shodex (registered trade mark of Showa Denko K.K.) Silica C18 M 4D |
| Mobile phase: | acetonitrile/water = 40/60 |
| Flow rate: | 1.0 mL/min |
| Detector: | ultraviolet absorption detector |
| Measuring wavelength: | UV 254 nm |
| Amount of sample injected: | 20 $\mu$L |

Conditions for Measurement by High Performance Chromatograph 2

| | |
|---|---|
| Column: | Shodex (registered trade mark of Showa Denko K.K.) Protein KW-803 |
| Mobile phase: | 100 mM sodium phosphate buffer solution (pH 6.5) |
| Flow rate: | 1.0 mL/min |
| Detector: | ultraviolet absorption detector |
| Measuring wavelength: | UV 280 nm |
| Amount of sample injected: | 20 $\mu$L |

The packing material for solid phase extraction of the present invention is a packing material ensuring excellent recovery obtained by adjusting the pore size of the packing material, which had not been taken into account in conventional packing materials. In particular, the packing material can easily concentrate a trace objective substance contained in an extra dilute solution in an environment-related sample or a medical sample, and at the same time, can easily remove impurities or contaminants present together. Accordingly, the packing material can facilitate various analyses with good precision and is effective in the field over a wide range, for example, in the measurement of harmful substances such as agricultural chemical in river water, the measurement of residual agricultural chemicals in farm products and the measurement of drugs in serum.

While the invention has been described in detail and with reference to specific embodiments thereof, it will be apparent to one skilled in the art that various changes and modifications can be made therein without departing from the spirit and scope thereof.

What is claimed is:

1. A packing material for solid phase extraction, comprising a particle having an exclusion limit molecular weight of from $1 \times 10^3$ to $1.5 \times 10^4$ in gel permeation chromatography using a standard polystyrene as the measuring sample, wherein the particle is obtained using a ratio of diluent to a total amount of monomers of 50 to 66.7%.

2. The packing material for solid phase extraction as claimed in claim 1, wherein the particle is a synthetic polymer particle obtained by polymerizing monomers containing at least a crosslinkable monomer.

3. The packing material for solid phase extraction as claimed in claim 2, wherein the synthetic polymer particle is a polymer of at least a crosslinkable monomer (A) and a non-crosslinkable monomer (B).

4. The packing material for solid phase extraction as claimed in claim 3, wherein an aromatic divinyl compound as the crosslinkable monomer (A) is in an amount of 30% by mass or more based on the total amount of monomers.

5. The packing material for solid phase extraction as claimed in claim 3, wherein a polyhydric alcohol poly(meth)acrylic acid ester as the crosslinkable monomer (A) is in an amount of 10% by mass or more based on the total amount of monomers.

6. The packing material for solid phase extraction as claimed in claim 4, wherein a polyhydric alcohol poly(meth)acrylic acid ester as the crosslinkable monomer (A) is in an amount of 10% by mass or more based on the total amount of monomers.

7. The packing material for solid phase extraction as claimed in claim 3, wherein an N-vinylcarboxylic acid amide as the non-crosslinkable monomer (B) is in an amount of 5 to 60% by mass based on the total amount of monomers.

8. The packing material for solid phase extraction as claimed in claim 4, wherein an N-vinylcarboxylic acid amide as the non-crosslinkable monomer (B) is in an amount of 5 to 60% by mass based on the total amount of monomers.

9. The packing material for solid phase extraction as claimed in claim 5, wherein an N-vinylcarboxylic acid amide as the non-crosslinkable monomer (B) is in an amount of 5 to 60% by mass based on the total amount of monomers.

10. The packing material for solid phase extraction as claimed in claim 7, wherein the N-vinylcarboxylic acid amide is N-vinylacetamide.

11. The packing material for solid phase extraction as claimed in claim 8, wherein the N-vinylcarboxylic acid amide is N-vinylacetamide.

12. The packing material for solid phase extraction as claimed in claim 9, wherein the N-vinylcarboxylic acid amide is N-vinylacetamide.

13. The packing material for solid phase extraction as claimed in claim 1, which is packed into a column, a cartridge or a reservoir.

14. The packing material for solid phase extraction as claimed in claim 1, which is used for concentrating an objective component and/or removing impurities or contaminants.

15. The packing material for solid phase extraction as claimed in claim 1, wherein the particle has an average particle size of 1 to 200 $\mu$m.

* * * * *